(12) United States Patent
Zanzucchi et al.

(10) Patent No.: US 7,427,377 B2
(45) Date of Patent: Sep. 23, 2008

(54) ANALYTE CONCENTRATION DETECTION DEVICES AND METHODS

(75) Inventors: Peter J. Zanzucchi, Princeton Junction, NJ (US); Sterling E. McBride, Princeton, NJ (US); Alexei Guennadievich Tsekoun, Princeton, NJ (US)

(73) Assignee: Intuity Medical, Inc., Sunnyvale, CA (US)

( * ) Notice: Subject to any disclaimer, the term of this patent is extended or adjusted under 35 U.S.C. 154(b) by 0 days.

(21) Appl. No.: 11/125,107

(22) Filed: May 10, 2005

(65) Prior Publication Data

US 2005/0202567 A1    Sep. 15, 2005

Related U.S. Application Data

(63) Continuation of application No. 10/394,230, filed on Mar. 24, 2003, now Pat. No. 7,052,652.

(51) Int. Cl.
*G01N 21/00* (2006.01)
*G01N 30/96* (2006.01)
*A61K 9/22* (2006.01)
*G01F 17/00* (2006.01)
*B65D 81/00* (2006.01)

(52) U.S. Cl. .................. 422/82.05; 604/890.1; 422/69; 702/55; 600/575

(58) Field of Classification Search ................. 442/100; 604/890.1; 702/55; 600/575; 422/82.05–100, 422/82.11
See application file for complete search history.

(56) References Cited

U.S. PATENT DOCUMENTS 3,092,465 A   6/1963   Adams, Jr.
3,630,957 A   12/1971  Rey
3,723,064 A   3/1973   Liotta
4,042,335 A   8/1977   Clement
4,637,403 A   1/1987   Garcia et al.
4,815,843 A   3/1989   Tiefenthaler et al.

(Continued)

FOREIGN PATENT DOCUMENTS

WO    97/30344    8/1997

(Continued)

OTHER PUBLICATIONS

Siu-Chun Lee, "Light Scattering by Closely Spaced Parallel Cylinders Embedded In a Finite Dielectric Slab", J. Opt. Soc. Am., A/vol. 16, No. 6, Jun. 1999, pp. 1350-1361.

(Continued)

*Primary Examiner*—Jill Warden
*Assistant Examiner*—Lore Ramillano
(74) *Attorney, Agent, or Firm*—Buchanan Ingersoll & Rooney PC

(57) ABSTRACT

Arrangements for the detection of the presence and/or concentration of an analyte in a sample of bodily fluid include diffuse transmission, diffuse reflection and edge or waveguide illumination arrangements. A vertical flow assay arrangement and/or technique is also disclosed, and includes a detection component that can be in the form of an array of optical detection elements. A number of assay pad constructions are described which may include at least one or more of the following components: a prefilter component, a reflective component, a membrane component, a reagent component, a mesh component, and a component to prevent lateral spreading.

18 Claims, 8 Drawing Sheets

U.S. PATENT DOCUMENTS

| | | | |
|---|---|---|---|
| 4,887,306 A * | 12/1989 | Hwang et al. ............... | 382/261 |
| 4,935,346 A | 6/1990 | Phillips et al. | |
| 5,223,219 A | 6/1993 | Subramanian et al. | |
| 5,508,200 A | 4/1996 | Tiffany et al. | |
| 5,701,181 A | 12/1997 | Boiarski et al. | |
| 5,841,126 A | 11/1998 | Fossum et al. | |
| 5,846,837 A | 12/1998 | Thym et al. | |
| 5,968,765 A | 10/1999 | Grage et al. | |
| 6,097,831 A * | 8/2000 | Wieck et al. ............... | 382/128 |
| 6,206,841 B1 | 3/2001 | Cunningham et al. | |
| 6,241,862 B1 | 6/2001 | McAleer et al. | |
| 6,268,162 B1 | 7/2001 | Phillips et al. | |
| 6,271,045 B1 | 8/2001 | Douglas et al. | |
| 6,555,061 B1 | 4/2003 | Leong et al. | |
| 6,558,624 B1 * | 5/2003 | Lemmon et al. ............. | 422/69 |
| 6,847,451 B2 | 1/2005 | Pugh | |
| 2003/0012693 A1 * | 1/2003 | Otillar et al. ................. | 422/58 |
| 2003/0083685 A1 | 5/2003 | Freeman et al. | |
| 2003/0153900 A1 * | 8/2003 | Aceti et al. ............. | 604/890.1 |
| 2003/0175987 A1 * | 9/2003 | Verdonk et al. ............ | 436/172 |
| 2004/0092842 A1 | 5/2004 | Boecker et al. | |

FOREIGN PATENT DOCUMENTS

| | | |
|---|---|---|
| WO | 00/42422 | 7/2000 |
| WO | WO0200101 A2 * | 2/2002 |

OTHER PUBLICATIONS

Textbook of Clinical Chemistry, N.W. Tietz, W.B. Saunders Company, 1986, pp. 1533 and 1556.

P. Trinder, "Determination of Glucose in Blood Using Glucose Oxidase with an Alternative Oxygen Acceptor" Ann. Clin. Biochem., 6 (1969), pp. 24-27.

H.M. Princen, "Capillary Phenomena in Assemblies of Parallel Cylinders—I. Capillary Rise Between Two Cylinders", Journal of Colloid and Interface Science, vol. 30, No. 1, May 1989, pp. 69-75.

H. M. Princen, "Capillary Phenomena in Assemblies of Parallel Cylinders—II. Capillary Rise in Systems with More Than Two Cylinders", Journal of Colloid and Interface Science, vol. 30, No. 3, Jul. 1969, pp. 359-371.

W. L. Clarke et al., "Evaluation of a New Reflectance Photometer For Use in Home Blood Glucose Monitoring", Diabetes Care, vol. 4, No. 5, Sep.-Oct. 1981, pp. 547-550.

W. E. Neeley et al., "An Instrument for Digital Matrix Photometry", Clinical Chemistry, vol. 27, No. 10, 1981, pp. 1665-1668.

W. E. Neeley, "Multilayer Film Analysis for Glucose in 1-μL Samples of Plasma", Clinical Chemistry, vol. 29, No. 12, 1983, pp. 2103-2105.

W. E. Neeley, "A Reflectance Photometer with a Square Photodiode Array Detector for Use on Multilayer Dry-Film Slides", Clinical Chemistry, vol. 34, No. 11, 1988, pp. 2367-2370.

W. E. Neeley, Reflectance Digital Matrix Photometry, Clinical Chemistry, vol. 29, No. 6, 1983, pp. 1038-1041.

* cited by examiner

ANALYTE CONCENTRATION DETECTION DEVICES AND METHODS

The present application is a continuation of U.S. patent application Ser. No. 10/394,230 filed Mar. 24, 2003, the content of which is incorporated herein by reference, in its entirety.

FIELD OF THE INVENTION

The present invention is directed to techniques and devices for detection of the presence and/or concentration of an analyte.

BACKGROUND OF THE INVENTION

A survey of the prior art reveals that numerous techniques and devices for performing an assay to determine the presence and/or concentrate of an analyte have been developed.

SUMMARY OF THE INVENTION

According to the present invention, the state of the art has been advanced through the provision of devices and techniques such as those described further herein, for accurately, efficiently, and economically determining the presence and/or concentration of an analyte. According to the present invention, the state of the art has been advanced, especially, but not exclusively, within the context of personal glucose monitoring devices and techniques.

According to one aspect, the present invention provides a device for monitoring the concentration of an analyte present in bodily fluid, the device comprising a detector, the detector comprising a sensor, the sensor comprising a CMOS sensor, a CCD sensor, or a photodiode.

According to a further aspect, the present invention provides a device for conducting an assay to determine the concentration of an analyte in a sample of bodily fluid, the device comprising: a sample collection channel having a bottom with at least one opening; an assay pad in communication with the at least one opening of the channel, the assay pad comprising a reagent adapted to produce a chemical reaction when exposed to the analyte, the chemical reaction producing a color change in the assay pad; and a linear array of CMOS optical detectors disposed relative to the assay pad so as to detect the color change.

According to a further aspect, the present invention provides an assay pad construction comprising: a first component comprising a constituent to separate red blood cells from plasma and further comprising a diffuse reflective material constituent; a second component comprising a chemical reagent; and a third component comprising a polyamide-containing mesh.

According to yet another aspect, the present invention provides an assay pad comprising: a first component comprising a diffuse reflective material; a second component comprising a hydrophilic material; a third component comprising a reagent; and a fourth component comprising a mesh or a membrane.

According to another aspect, the present invention provides a method of performing an assay to determine the concentration of an analyte in a sample of bodily fluid, the method comprising: (i) providing a sample collection channel having a first volume; (ii) introducing a sample of bodily fluid into the channel, the sample introduced into the channel having a second volume which is less than the first volume; (iii) vertically conveying the sample from the channel onto an assay pad; (iv) reacting the analyte in the sample with a chemical reagent in the assay pad thereby producing a color change in the assay pad; and (v) detecting the color change with a linear array of CMOS sensors by detecting the color change with each individual CMOS sensor in the array which is incident upon the area of color change in the assay pad.

According to still another aspect, the present invention provides a method of determining an estimated volume of a sample of bodily fluid being subjected to an assay, the method comprising: (i) providing an elongated sample collection channel having a volume directly proportional to its length; (ii) introducing a sample of bodily fluid into the channel; (iii) vertically conveying the sample from the channel onto an assay pad; (iv) reacting the analyte in the sample with a chemical reagent in the assay pad thereby producing a color change in the assay pad; (v) disposing a linear array of CMOS sensors incident to the assay pad for detecting the color change, the length of the CMOS array being commensurate with the length of the collection channel; (vi) detecting the color change with each individual CMOS sensor in the array which is incident upon the area of color change in the assay pad; and (v) calculating the estimated volume of the sample in the collection chamber based upon the number of sensors in the linear array which detect the change in color.

DETAILED DESCRIPTION OF THE INVENTION

Figure 1:
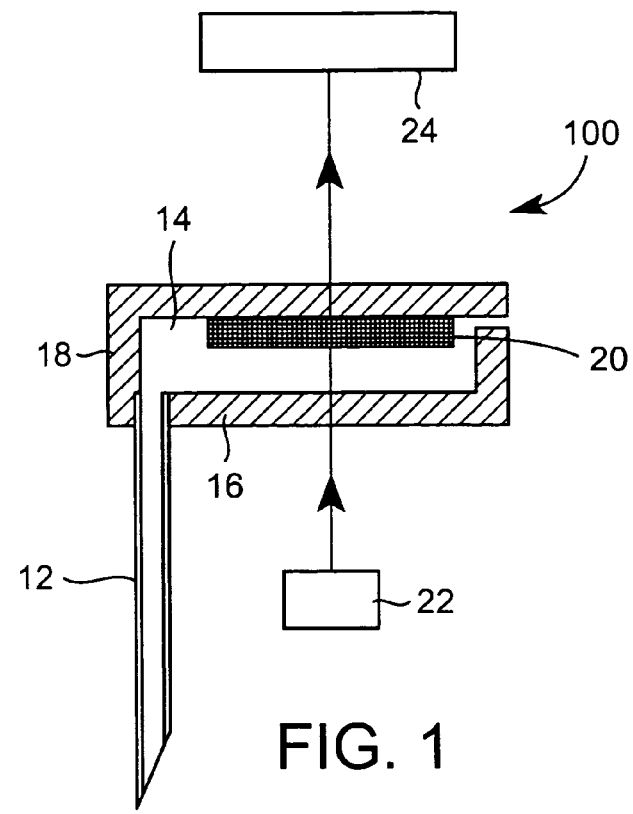
FIG. 1 is a schematic illustration of an analyte detection arrangement according to the present invention.

Exemplary arrangements for the detection and measurement of the presence and/or concentration of an analyte, such as glucose, will now be described by reference to the drawing figures.

FIG. 1 is one such arrangement 100 for the optical detection of the presence and/or concentration of an analyte such as glucose. The arrangement 100 can generally be described as a diffuse transmission arrangement.

According to this embodiment of the present invention, the substance to be analyzed is transported via a conduit 12. When the substance to be analyzed comprises a sample of whole blood, interstitial fluid, or mixture thereof, the conduit 12 can be in the form of a hollow member or needle. The needle can be of a very narrow gage, or a so-called microneedle. Such a needle typically having a size on the order of 40-100 micrometers.

The microneedle may also act as a skin penetration member as well as a conduit. Alternatively, the skin penetration member may be in the form of a solid lancet (not shown), which acts to produce a sample of bodily fluid which is then transported via conduit, e.g.—12.

The substance to be analyzed is transported via the conduit 12 to a chamber 14. The chamber may have any suitable form. According to one embodiment, the chamber 14 is formed by a lower member 16 and an upper member 18. These members 16, 18 can be constructed to allow light to be transmitted therethrough.

An assay pad 20 is provided within the chamber 14. The pad 20 receives the substance to be analyzed. The pad 20 is provided with a substance that reacts with the analyte. The results of this reaction is detectable and the data generated through detection is used to determine the presence and/or concentration of the analyte. According to the principles of the present invention, the pad 20 is provided with a construction to achieve this objective, and others. A discussion of the specifics of the pad 20 will be deferred.

A light source 22 can be provided so as to produce light that is incident upon a first side of the pad 20. Any suitable light source is envisioned. According to a preferred embodiment, the light source comprises a light emitting diode (LED). The LED or light source 22 can provide incident light of any suitable wavelength. Wavelengths on the order of 500-700 nm are suitable. For example, incident light with a wavelength on the order of 670 nm may be transmitted from light source 22. At approximately 670 nm, absorption of the incident light by hemoglobin tends to be reduced.

An optical detector 24 is positioned so as to receive light transmitted through a second side of the pad 20, the second side being opposite the first side. The optical detector can be a digital imaging device, such as a complementary metal oxide semiconductor (CMOS) device, a charge couple device (CCD), or any photodiode. The imaging device may comprise and array of individual detectors.

According to the present invention, the implementation of digital imaging devices permits the analysis of samples that are not of uniform volume. This is accomplished at least in part by the ability of individual detectors to take readings, which are then averaged or combined to generate an overall reading. The larger the sample, the larger the "spot" formed on the pad 20, and the more individual detectors pick up a reading of the reaction occurring in the pad 20. Thus, unlike assays performed by conventional personal glucose monitoring devices and the like, the assay of the present invention is not dependent upon the volume of the sample being analyzed. When an assay is incorporated into a monitoring device wherein the monitoring is performed in an automated fashion, the user is often unable to determine if a sample of body fluid of a particular volume has been obtained. In conventional assays, the accuracy of the assay is directly linked to a specific volume of sample undergoing analysis (e.g.—"microtitration"). The present invention breaks this dependence, thereby providing robust and reliable devices, such as personal glucose monitoring devices, that can function effectively over a range of potential sample volumes. Other details of the detector 24, and associated components, will be deferred to later text.

The arrangement 100 may be incorporated into a larger overall device. According to one embodiment, the arrangement 100 is incorporated into a personal glucose-monitoring device. According to one alternative, the device is ambulatory. The arrangement 100 can be incorporated into devices, such as the ones described in U.S. Patent Publication No. U.S. 2002/0087056 or U.S. 2003/0153900, both of which are incorporated herein by reference in their entirety.

In the following description of alternative arrangements, those elements that correspond to features already described in previous arrangement(s) have been designated with the same reference numbers.

Figure 2:
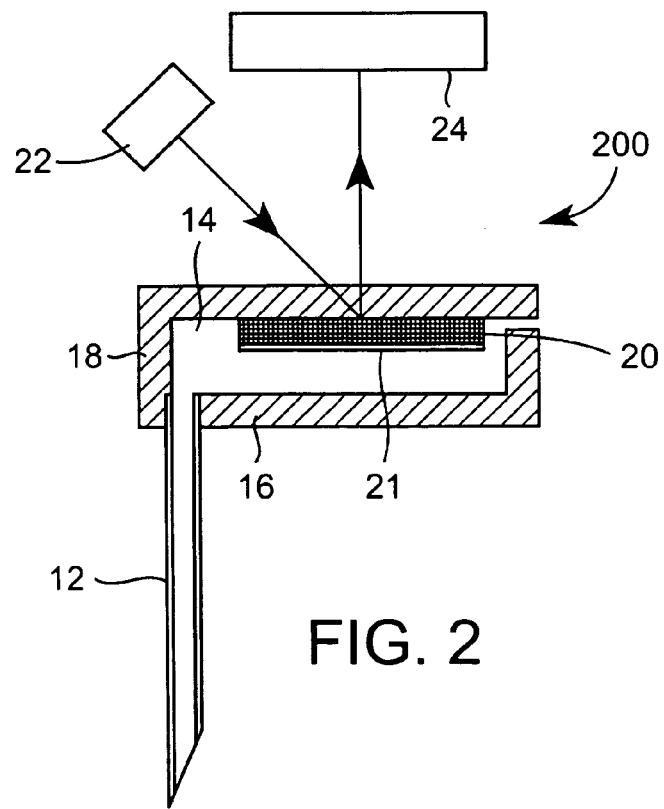
FIG. 2 is a schematic illustration of an analyte detection arrangement according to another aspect of the present invention.

An alternative arrangement 200 is depicted in FIG. 2. The arrangement 200 can generally be described as a diffuse reflection arrangement.

While arrangement 200 is similar to the previously described arrangement 100, the light source 22 is provided such that it transmits light which is incident upon a first side of the assay pad 20. At least a portion of this incident light is reflected off of the first side. This reflected light can then be collected by the optical detector 24, which is disposed on the same side as the light source 22, relative to the test pad 20. Preferably, the light source 22 and the optical detector 24 are disposed, relative to the reaction chamber, on a side which is opposite from the side of the reaction chamber into which the conduit 12 introduces the substance to be analyzed. This orientation is shown in FIG. 2.

In order to improve reflection of the incident light from the test pad, the test pad 20 may be provided with a blocking layer 21. Such a layer can be formed of any suitable material, such as zirconium oxide or titanium oxide.

Since only one side of the test pad is read by the detector, the reading taken by the detector 24 is insensitive to the contents of the chamber 14 since the contents of the chamber 14 are not in direct communication with the side of the test pad 20 being read.

Figure 3:
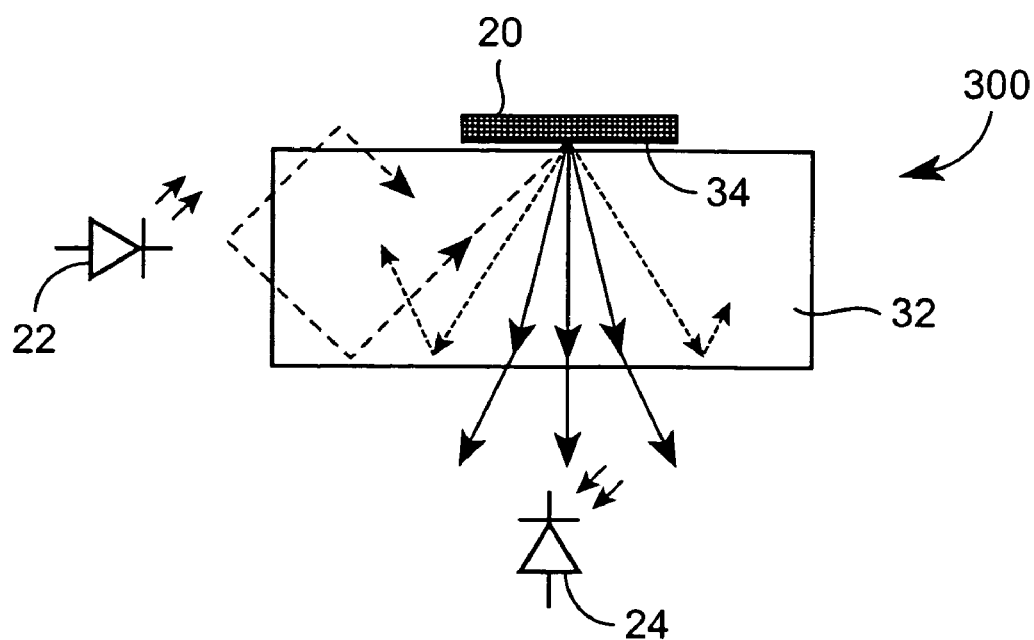
FIG. 3 is a schematic illustration of an analyte detection arrangement according to a further aspect of the present invention.

Another alternative arrangement constructed according to the principles of the present invention is illustrated in FIG. 3. The arrangement 300 can generally be described as an edge or waveguide illumination arrangement.

According to this aspect of the present invention, a light source 22 is arranged such that a diverging light beam strikes an edge of a transparent waveguide member 32, and couples the transmitted light inside the waveguide, as illustrated by the broken lines contained in FIG. 3.

When the angle of incident light is greater than a critical angle of incidence, "$\theta_C$", losses of incident light due to reflection are minimized. This critical angle can be expressed as $\theta_C = \sin^{-1}(n_2/n_1)$, where $\theta_C$ is the angle of incidence that will cause incident light to become trapped in the waveguide, and $n_2$ and $n_1$ are the indices of refraction for a first material and a second material that define a boundary across which the light is attempting to travel (e.g.—air and test strip material).

In order to further minimize such losses, the coupling edge of the waveguide may be treated with an anti reflective coating or an index-matching medium. For example, one or more thin layers of silicon oxide may be applied to the coupling edge. A thickness of approximately 200 nm is an exemplary thickness.

Light trapped inside the waveguide propagates by total internal reflection (TIR) until it encounters the assay pad 20 which is affixed to or in communication with a surface of the waveguide, as illustrated in FIG. 3. The assay pad 20 is provided with a surface in communication with the reflected light inside the waveguide, which is light scattering. Light impinging on this surface 34 of a test pad 20 is scattered at all angles. As illustrated by the dotted lines in FIG. 3, some of the light is scattered at a large angle relative to the normal of surface 34. This light is also trapped inside the waveguide. However, some of the light is scattered at a relatively small angle compared to the normal of surface 34, as illustrated by the solid double arrow lines of FIG. 3, and is consequently transmitted outside of the waveguide and received by the detector 24.

Figure 4:
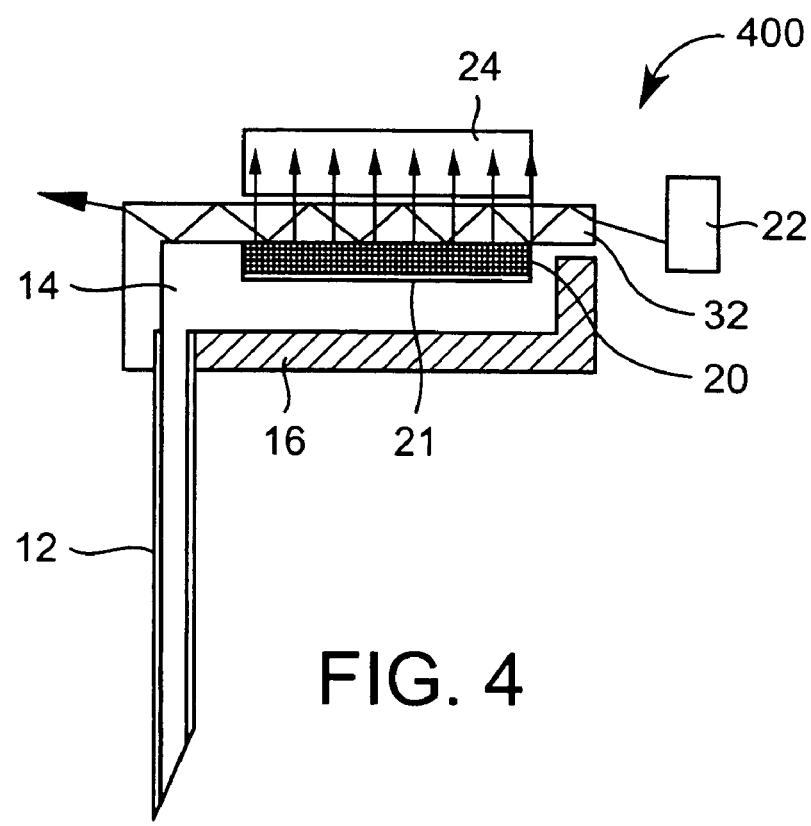
FIG. 4 is a schematic illustration of an analyte detection arrangement according to another aspect of the present invention.

Another arrangement 400 of the type described above, is also illustrated in FIG. 4. As illustrated in FIGS. 3 and 4, arrangements of this type (300, 400) are such that light provided by the light source 22 is incident upon the waveguide at a relatively small angle to the surface thereof, a larger amount of this incident light is transmitted through the waveguide, when compared with arrangements wherein the incident light is provided at a relatively steep angle to the incident surface. Thus, when the light source is an LED-type source, less power is required in order to provide the necessary amount of incident light to perform the assay, and power consumption can be minimized.

The light source 22 can be closely aligned with the edge of the waveguide 32, and thus may provide for a compact configuration. In addition, the detector element 24 can be positioned in close proximity to the waveguide 32, assay pad 20 and light source 22 (FIG. 4), thereby enabling it to be more protected from stray light sources.

Figure 5:
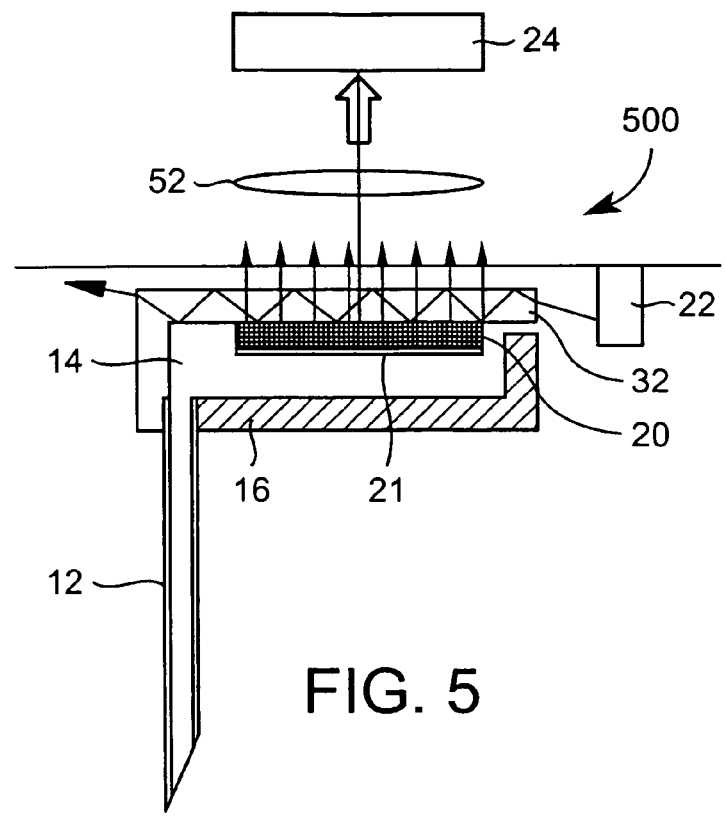
FIG. 5 is a schematic illustration of an analyte detection arrangement according to a further aspect of the present invention.

In certain instances, it may be desirable to provide an arrangement 500 as depicted in FIG. 5. In this arrangement 500, an imaging lens 52 is provided and disposed such that it captures and focuses light reflected from the assay pad 20 toward the optical detector 24. The lens 52 may comprise a refractive or defractive element (Fresnel lens).

In FIG. 5, the lens 52 is utilized in connection with an edge illumination-type arrangement.

Although the lens 52 is illustrated as being disposed at some distance from the waveguide 32 which forms the upper portion of the reaction chamber 14, the lens member may also be integrated into either the surface of the detector 24, or into the upper member (e.g.—18, FIG. 1) or waveguide 32.

Figure 6:
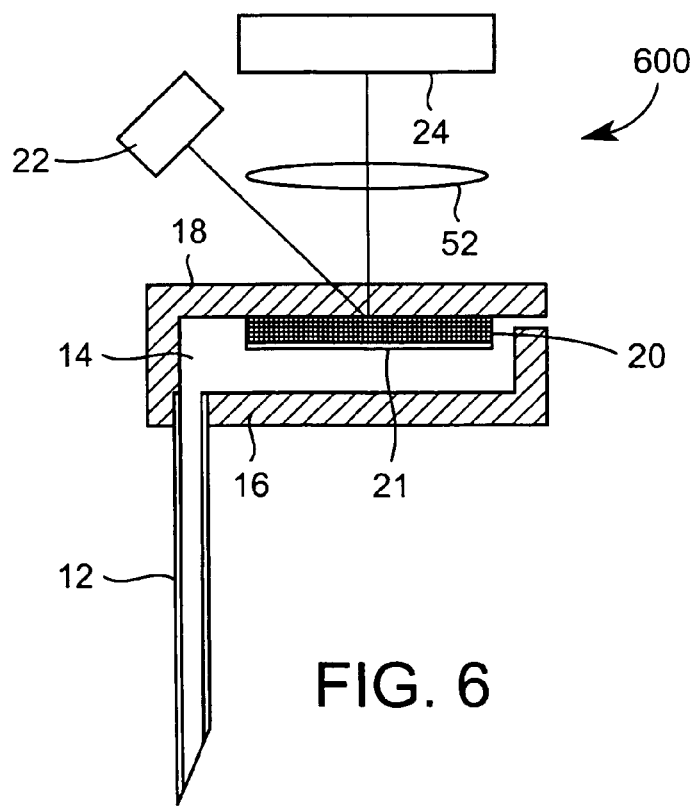
FIG. 6 is a schematic illustration of an analyte detection according to another aspect of the present invention.

FIG. 6 depicts an alternative arrangement 600 which comprises a diffuse reflection type arrangement which incorporates an imaging lens member 52, as described above.

Figure 7:
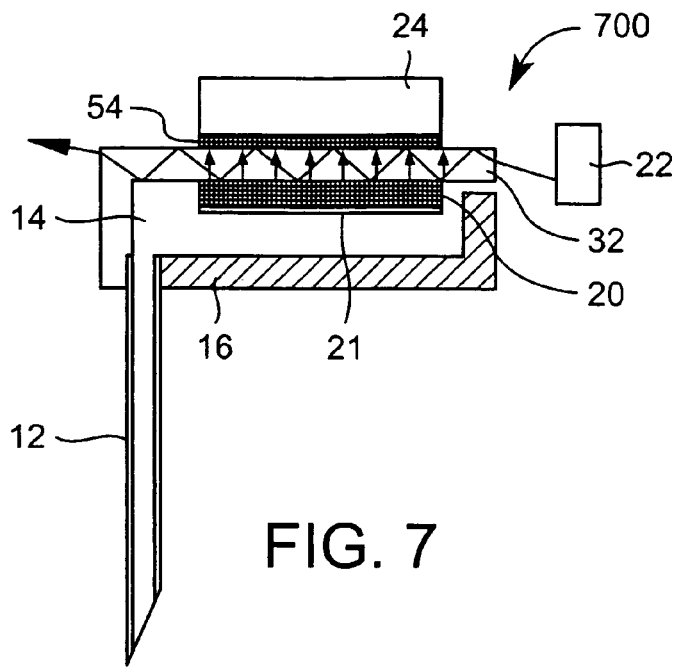
FIG. 7 is a schematic illustration of an analyte detection arrangement according to a further aspect of the present invention.

Another arrangement 700 is depicted in FIG. 7. The arrangement 700 includes an edge-illumination type arrangement including waveguide 32. An imaging lens 54 is also included. In this arrangement, the imaging lens is integrated into either the waveguide 32 or the detector 24.

Figure 8A:
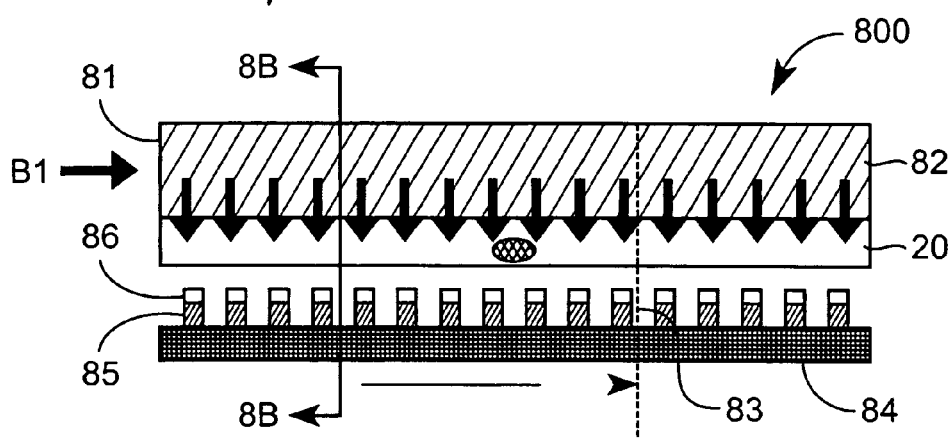
FIG. 8A is a schematic illustration of an assay arrangement and technique according to the present invention.
Figure 8B:
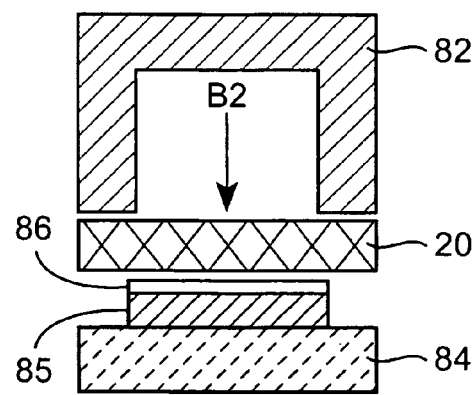
FIG. 8B is a cross-section of FIG. 8A taken along line 8B-8B.

FIGS. 8a and 8b illustrate in further detail certain aspects of an additional embodiment of the present invention. FIGS. 8a and 8b illustrate and arrangement 80 which can be generally described as a vertical-flow assay.

The arrangement 800 includes a channel member 82 having an open "bottom", an assay pad 20 in communication with the open bottom of channel member 82, and an optical detector, preferably in the form of an array 84 of digital imaging devices 85. According to one preferred aspect of the invention, lens elements 86 are incorporated into the arrangement.

Although lens elements 86 are illustrated as being in the form of discrete individual lenses in close proximity to the individual detector elements or pixels 85, it is within the scope of the present invention that alternative constructions are possible. For example, the lenses 86 could be spaced from the detectors 85, and/or a single integrated lens construction could be utilized instead of discrete lenses 86.

As previously noted, arrangements of the type depicted in FIGS. 8a and 8b permit the reliable and effective analysis of relatively small amounts of substances, which is not dependent upon a particular repeatable volume.

The channel member 82 is elongated. In other words, the substance being analyzed, such as a sample of body fluid is introduced at one end 81 of the channel member 82 and flows laterally or axially therethrough. The substance being analyzed then permeates the test pad 20 disposed thereunder. While the open channel member 82 defines a particular volume, it is not necessary to completely fill the channel member 82 in order to conduct an accurate analysis. For example, as illustrated in FIG. 8A, a particular volume of substance to be tested may only partially fill channel member 82, for example, it may only fill channel member 82 up to the point defined along line 83. When conducting an analysis, the independent detector pixels 85 of the array 84 on the left-hand side of line 83 are activated and will take a reading from the analysis side of the test pad 20 once the analyte present in substance under analysis reacts with the chemicals contained in the test pad 20. Those individual detector elements of the array which are on the left-hand side of line 83 will generate a signal which is indicative of the presence of this reaction. Those individual detector elements 85 of array 84 which are on the right hand side of line 83 will not generate such a reading. Thus, the readings or data generated by each individual detector element 85 of the array 84 is taken and analyzed, such as by averaging, to generate an overall reading of the presence and/or concentration of a particular analyte contained in the substance under analysis.

Moreover, since the volume of the channel member 82 is known, and the length of the detector element contained in the array 84, as well as any correction due to the presence of lens elements 86 are known, the volume of the sample under analysis can be estimated based upon the number of pixels which detect the reaction between the analyte and the chemical reagents contained in test pad 20. An exemplary, non-limiting embodiment will now be described to further illustrate the principles of the present invention.

The time between the readings taken by the detectors 85 of the array 84 can also be monitored by the electronics of the arrangement. The specific means of implementing this monitoring being well within the skill of those in the art. Thus, the arrangement of the present invention can also analyze the kinetics of the reaction between the analyte and the chemical reagents, thereby offering the possibly to provide additional useful information that can be used to provide an insightful analysis of the sample.

An arrangement 80 of the type depicted in FIGS. 8a through 8b can advantageously be utilized to analyze very small volumes of a substance to be tested. For example, the arrangement can be utilized to assay 1-500 nanoliter (nL) volumes. The substance to be tested may include whole blood, interstitial fluid, or combinations thereof.

Assuming a nominal 250 nanoliter maximum volume, a sample of body fluid is introduced along direction $B_1$ from the right hand side 81 of channel number 82 through any suitable means, such as conduit 14 (see, e.g.—FIGS. 1 through 2). The sample is extended laterally into the elongated channel member 82. The sample is extended over a relatively long length, which can be on the order of a few millimeters. According to one specific example, the channel is approximately 250 micrometers (width)×140 micrometers (height)×7,000 micrometers (length). The sample of body fluid then flows vertically along direction $B_2$ through the open bottom portion of channel 82 and into the assay pad 20. A color change in the assay pad 20 may be produced by a chemical reaction triggered by the presence of a specific analyte contained in the sample of body fluid, such as glucose. This color change can be detected on the opposite of the assay pad from which the sample of body fluid is introduced. This color change is detected by a suitable detection device, such as the optical detector array 84, which may be composed of a plurality of digital imaging detectors 85. According to one aspect, these digital detectors comprise either a CMOS, CCD, or photo diode array.

As a sample body fluid, such as whole blood, flows vertically through the test pad 20, red blood cells can be filtered or blocked from the opposite side of the test pad 20, which is generally viewed as being preferable so as to enable a more accurate reading of the levels of analyte present in the sample. The chemical reagents and dye products utilized in test pad 20 can be chosen from any number of well know substances. In any event, these chemistries should provide a discernable and readable reaction over an appropriate range of analyte concentration levels. In the case where the device is to be utilized to monitor the concentration of glucose contained in samples which comprise mainly whole blood, these chemistries should be able to produce reactions which can then be detected to indicate a glucose concentration ranging from, for example, 40-500 mg/dL.

According to a preferred aspect, the detector array 84 is formed from a plurality of individual CMOS-type detectors 85. CMOS detectors are less costly than other types of digital imaging devices. As described above, due to the time-dependent aspect of the arrangement 80, which may include CMOS detectors 85, various "clock" or time-driven electronic devices may be incorporated. Data can be taken from the detectors 85 and fed to such devices (directly or from storage) thereby enabling the monitoring and interpretation of the kinetics and other aspects of the reaction between the analyte and the reagent.

By the utilization of an array 84 of individual detectors 85, uniformity and accuracy of the assay is also promoted. For example, readings are taken and utilized from multiple individual detector elements, or pixels, are less susceptible to variations in uniformity of the materials of the assay pad, or other localized abnormalities, which can be accounted for and corrected by the interpretation and manipulation of the data generated by the individual pixels 85 of the detector array 84. For example, statistical analyses and associated algorithms may be used to correct for such localized defects, and therefore improve the accuracy of the overall reading generated by the device.

Figure 9:
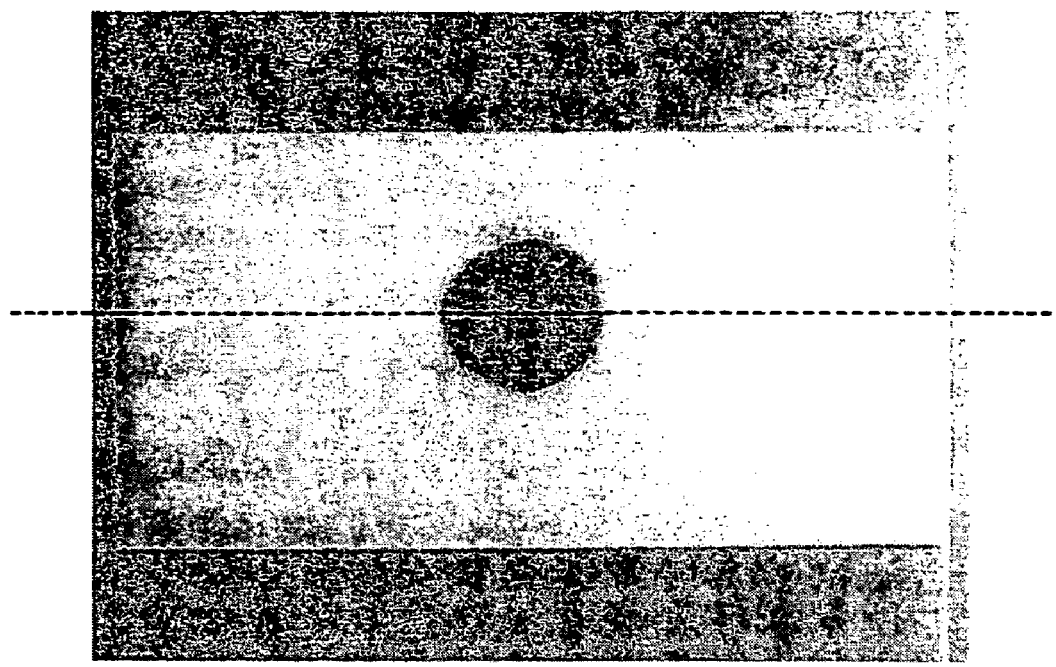
FIG. 9 is picture of an exemplary reaction spot according to the present invention.
Figure 10:
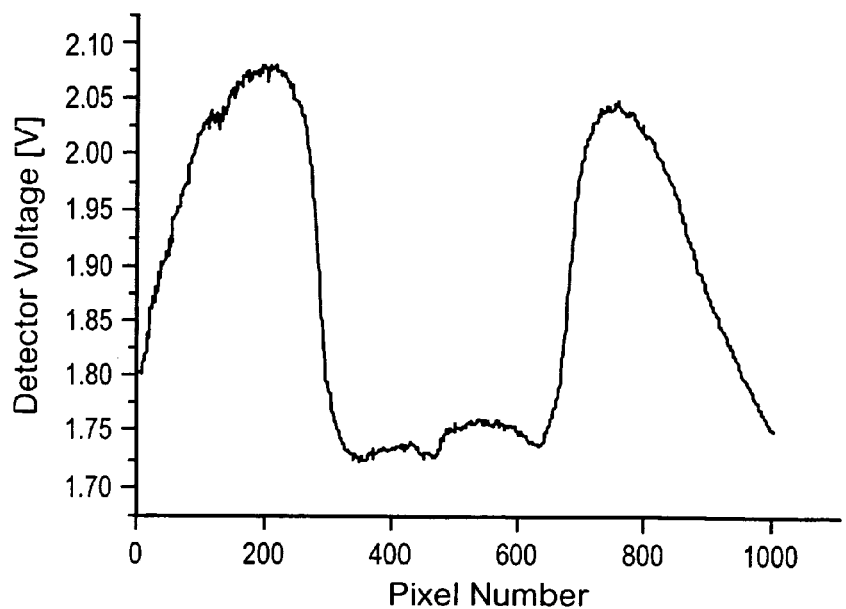
FIG. 10 is a scan along the dashed line of FIG. 9.

FIGS. 9 and 10 represent a scan performed by an arrangement 80 such as the one depicted in FIGS. 8a and 8b. FIG. 9 is a picture of a test spot formed on a commercially-available assay pad. FIG. 10 is a plot of the signal generated by an array of detector elements 84 as they are scanned along the dashed line contained in FIG. 9. As illustrated in FIG. 10, the lower voltage readings correspond to the area occupied by the test spot of FIG. 9 along the dashed line.

Figure 11:
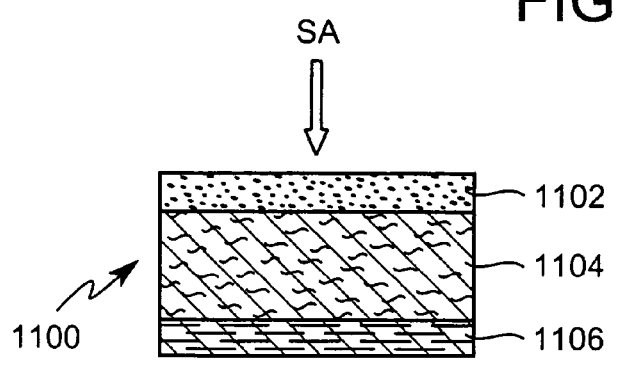
FIG. 11 is a schematic illustration of a layered test strip constructed according to the present invention.

FIG. 11 is a schematic illustration of one possible construction for the assay pad 20. The assay pad construction 1100 has a sample application side SA as well as an analysis side A. According to one construction, the assay pad 1100 is composed of at least 3 constituent components: a blocking component 1102; a membrane component 1104; and a chemical reagent component 1106. When the sample to be analyzed is composed at least in part of whole blood, red blood cells are separated from the plasma, which is then transported to the reagent component 1106 which includes enzymatic chemistries selected to produce a chemical reaction with one or more analytes present in the sample.

The blocking component 1102 may include an agent to filter or pre-filter red blood cells. By way of example, the blocking component 1102 may include zirconium oxide ($ZrO_2$).

The membrane component 1104 can be formed of any suitable material. For example, the membrane be a high light transmitting material, or optionally can be an opaque or substantially opaque material. Suitable materials may include styrene and/or nylon. The membrane component 1104 can be in woven or non-woven form. According to one aspect, the membrane is in the form of a woven mesh.

As indicated above, the reagent component 1106 is chosen according to its ability to react with the analyte under investigation. Any suitable reagent chemistry can be utilized. Specific examples of suitable material include a glucose oxidase (e.g.—from Biocatalysts product G575P), a soybean peroxidase (e.g.—from Organic Technologies, product 73930.1 medical diagnostic grade), an amino antipyrine hydrochloride (e.g.—from TCI, product A0257) and an Aniline derivative dye for a "Trinder" reaction (see, e.g.—P. Trinder, "Determination of Glucose in Blood Using Glucose Oxidase with an Alternative Oxygen Acceptor").

While the various constituent components of the assay pad construction 1100 are illustrated in FIG. 11 as distinct layers, it should be understood that the present invention is not limited to such a construction. For example, the blocking component 1102 and/or the reagent component 1106 may be partially or entirely subsumed and contained within the membrane component 1104. Thus, it is entirely possible that a surface "layer" of the blocking component 1102 and/or reagent component 1106 may be present. Alternatively, the blocking component 1102 and/or the reagent component 1106 may be entirely subsumed, contained or impregnated within the membrane component 1104, such that no distinct blocking component "layer" or reagent component "layer" is present at all.

It should be noted, that not only with respect to the embodiment depicted in FIG. 11, but as well as with all of the following alternative test strip constructions according to the present invention (e.g.—FIGS. 12-16), similar alternative constructions to that explicitly described above are comprehended within the scope of the present invention. For instance, the constituent components described herein are not limited to distinct "layers". Rather, one or more of the constituent components of the test strip constructions described herein may be partially, or entirely, subsumed, contained or impregnated within other constituent components of the test strip constructions and therefore not be present as distinct "layers".

With respect to the embodiment depicted in FIG. 11, the blocking component 1102 and/or reagent component 1106 may be applied to the membrane component 1104 in any suitable manner. For example, the blocking component 1102 and/or reagent component 1106 may be coated upon the membrane 1104. An example of suitable coating techniques includes spin coating.

Figure 12:
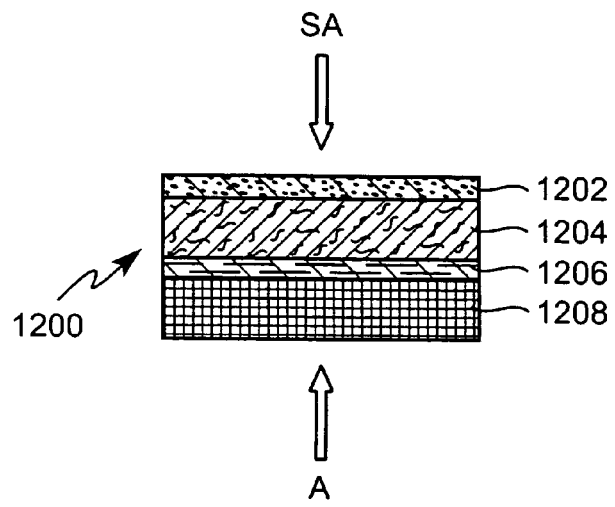
FIG. 12 is a schematic illustration of another layered test strip construction according to the present invention.
Figure 13:
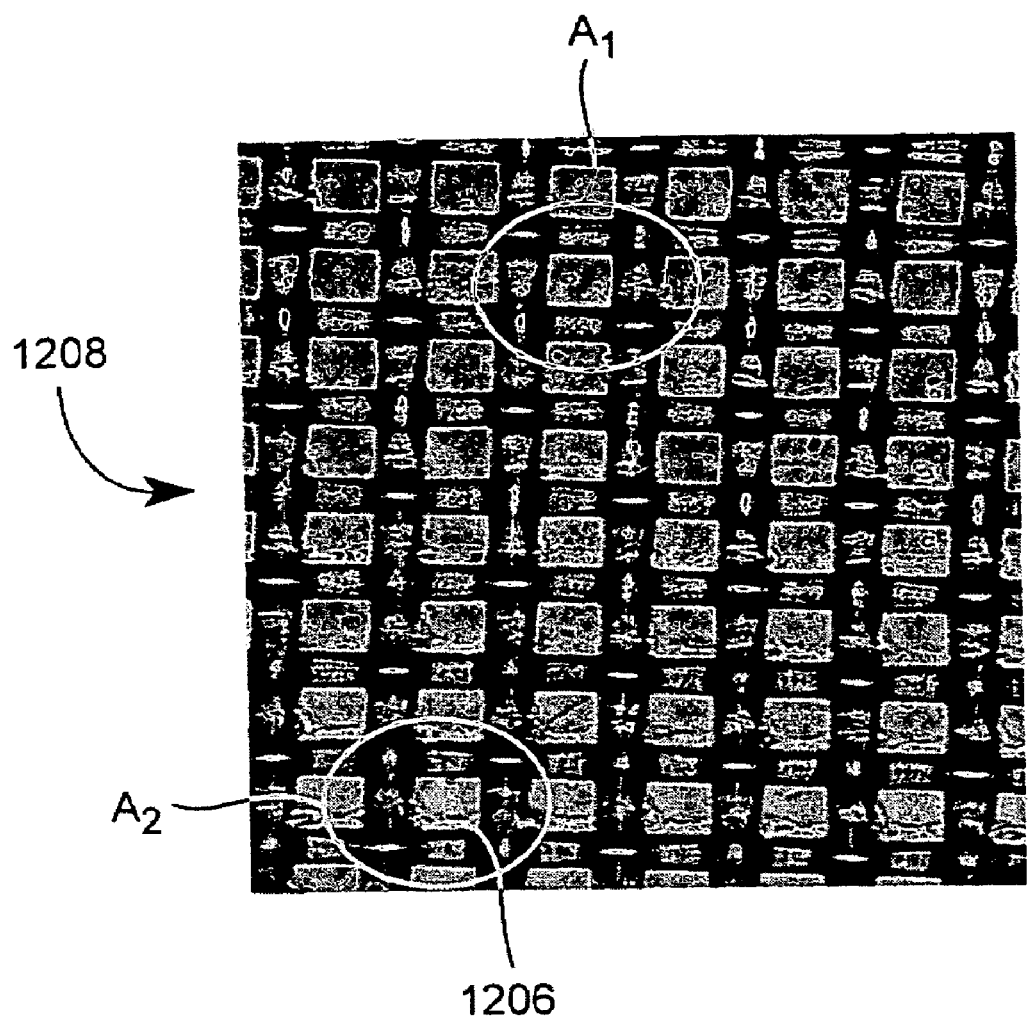
FIG. 13 is a picture of a mesh wherein at least a portion thereof includes retained reagent.

FIG. 12 illustrates one possible alternative construction 1200 for the assay pad 20. According to one construction, the assay pad construction 1200 is composed of at least 4 components: a prefilter and reflective component 1202, a membrane component 1204, a reagent component 1206, and a mesh component 1208. With the above-described structure, in the case where the substance to be analyzed is a sample which is composed at least in part of whole blood, the red blood cells are separated from the plasma, so that components 1202 and/or 1204 retain the red blood cells without lysis. The plasma is then vertically transported to the reagent component 1206 which includes enzymatic chemistries. These substances may include any suitable material, which are generally known in the art. Specific examples of suitable materials include a glucose oxidase (e.g.—from Biocatalysts product G575P), a soybean peroxidase (e.g.—from Organic Technologies, product 73930.1 medical diagnostic grade), an amino antipyrine hydrochloride (e.g.—from TCI, product A0257) and an Aniline derivative dye for a "Trinder" reaction (see, e.g.—P. Trinder, "Determination of Glucose in Blood Using Glucose Oxidase with an Alternative Oxygen Acceptor").

The component 1204 may comprise any suitable blood-filtering component or material. Some materials which have been used to separate red blood cells from plasma and samples of whole blood include glass fibers, mesh cloth, unwoven mats, asymmetric membranes, and porous polymers.

Regardless of what type of material is chosen for component 1204, the avoidance of spreading or lateral diffusion, which may occur with such materials as poly (ethersulfone) membranes, is desirable. An exemplary suitable material is, a hydrophilic poly(vinylidene fluoride) unwoven membrane. Such membranes are commercially available from the Millipore Corporation (e.g.—with 0.1 micron openings). Other suitable materials include unwoven membranes comprising a polyamide. Other materials may be incorporated to achieve various performance objectives, such as poly(acrylic acid) (PAA), hydroxyethyl cellulose, sodium alginate, and gelatin.

The pad 1200 may further include a component 1202, such as a prefilter and/or diffuse reflection component. Thus, the component 1202, when included, serves to improve separation of red blood cells from a sample containing whole blood, and/or increase the reflection of incident light upon the opposite side of the pad when undergoing optical analysis. Suitable materials for use as component 1202 include a zirconium oxide ($ZrO_2$), optionally combined with a polymer binder material. The component 1202 can be applied to the membrane, or component 1204, by using any suitable technique. One such suitable technique is spin coating. Spin coating promotes uniform distribution of the component 1202 onto and/or within the membrane component 1204. As previously explained, while components 1202 and 1204 have been illustrated as distinct layers, the component 1202 may be partially, or entirely contained within the membrane component 1204, thus effectively combining these two components into a single unitary member, rather than the illustrated distinct layers. When, according to the above-described alternative embodiment, the component 1202 comprises a prefilter and diffuse reflection material and a polymer binder, the presence of the polymer binder tends to form at least a thin layer or film over the membrane component 1204. This thin film may have any suitable thickness, for example, the component 1202 may partially permeate the membrane component 1204 and leave a thin film having a thickness on the order of less than 5 micrometers on top of the membrane component 1204.

The component 1206 comprises a reagent which may be formed from any suitable composition, such as the chemicals described above, and may optionally be provided in a binder of poly(acrylic acid), hydroxypropylmethylcellulose (HPMC) or similar polymers that reduce lateral spreading of the substrate or sample undergoing analysis.

The mesh component 1208 and the reagent 1206 component may also be integrated into a single layer or constituent element of the test pad 20. For example, reagent material 1206 can be coated onto the mesh component 1208. Any suitable coating technique may be utilized. A spin coating technique is one such technique for providing the reagent on the mesh component 1208 which allows for precise and relatively thin coating of the reagent component 1206 to be applied to the mesh component 1208. According to one construction, this "coating" is entirely absorbed and contained within mesh component 1208. The mesh component 1208 should be permeable to oxygen in order to promote the reaction of the analyte with the chemical reagent component 1206. According to one aspect, the mesh component 1208 can be formed from a high reflectance woven mesh, such as nylon. Thus, according to one aspect, mesh component 1208 is formed from an open polyamide or nylon mesh material. This nylon mesh material having a reagent incorporated therein is believed to increase the sensitivity of the assay. The open structure of the nylon mesh, in conjunction with the controlled amount of the reagent component material 1206 incorporated therein, increases the diffuse reflection of light incident thereon. This increased diffuse reflection is believed to be caused by the multiple reflections and increased path lengths provided by the open nylon mesh structure. According to one exemplary embodiment shown in FIG. 13, the mesh component 1208 has openings have a dimension which is on the order of 68 microns, and a filament diameter which is on the order of approximately 50 microns. The region indicated by circle $A_1$ illustrates the absence of reagent material within the mesh, wherein the reagent material has been consumed by chemical reaction with the analyte. Circle $A_2$ indicates an area of the mesh in which the reagent material is still disposed thereon.

The cylindrical fibers of the nylon mesh may scatter the light onto the external exposed layer or surface thereby introducing multiple reflection and increased path links. The scattering of incident light is largely dependent upon a refractive index of the cylinders which form the filaments of the mesh. The refractive index of nylon is relative large, on the order of 1.53, and this is beneficial. Moreover, the above-described application of the reagent component 1206 to the mesh component 1208 can simplify manufacture.

Figure 14:
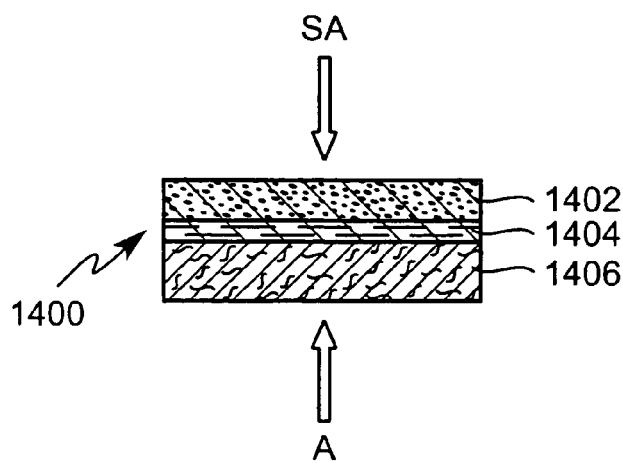
FIG. 14 is a schematic illustration of a further layered test strip construction according to the present invention.

Another alternative test pad or test strip construction 1400 is illustrated in FIG. 14. According to one aspect, the test pad construction 1400 includes three basic components: a filter and/or diffuse reflective component 1402, a chemical reagent component 1404, and a membrane component 1406. As previously discussed, a sample to be analyzed is applied to the sample application side SA of test pad 1400. When the sample contains, at least in part, whole blood, red blood cells are separated from the plasma by component 1402 and are transported to the reagent component 1404, which may be partially or entirely impregnated it the membrane component 1406.

The component 1402 may be formed from any suitable construction that provides filtration and/or diffuse reflection functions. For example, suitable constructions have been described above. According to one specific example, the component 1402 may comprise a zirconium oxide material combined with a permeable polymer binder material, such as HPMC, that limits lateral diffusion. Another suitable example includes a zirconium oxide material combined with a permeable polymer binder such as vinyl butyral. The zirconium oxide and polymer binder are combined in any suitable proportions, such as 20:80.

The reagent component 1404 includes at least one chemical reagent chosen to provide a suitable reaction with the analyte(s) under investigation. Any suitable reagent can be chosen. For example, the reagent may comprise a glucose oxidase, soy bean peroxidase, amino antipyrine hydrochloride, and/or aniline derivative dyes. The chemical reagent may optionally be combined with a binder component. When present, the binder component is preferably formed from a material which reduces the tendency for lateral spreading of the sample within the test pad 1400. Suitable examples binder material examples include HPMC and PAA.

A suitable membrane component 1406 can also be provided. According to one embodiment, the membrane component 1406 can comprise a fibrous unwoven material. One specific example includes a cellulose acetate unwoven fibrous membrane material.

Both the filter/diffuse reflective component 1402, as well as the reagent component 1404 can be applied to the membrane component 1406 by any suitable technique. According to one example, the reagent component 1404 is applied to the membrane component 1406 by a coating technique, such as spin coating. Reagent component 1404 may be partially, or entirely impregnated within the membrane component 1406. Thus, a thin film or layer of reagent component 1404 may be present on the top surface of the membrane component 1406 (i.e.—the side closest to the sample application side SA of the test pad 1400). When present, this thin top layer can be on the order of a few microns in thickness. Alternatively, the reagent component may be entirely subsumed, contained or impregnated within the membrane component 1406, such that no distinct layer is present on the top surface of the membrane component 1406 (i.e.—the surface of membrane 1406 which is closest to the surface application side SA of the pad 1400).

The filter/diffuse reflective component 1402 can then be applied subsequent to application of the reagent component 1404. The component 1402 can also be applied by any suitable technique, such as spin coating. According to one specific example, a filter/diffuse reflective component comprising a zirconium oxide and hydrophobic permeable polymer binder material is spin coated at approximately 1000 rpm onto the membrane/reagent components 1406/1404. The filter/diffuse reflective component 1402 may be partially impregnated within the membrane 1406, leaving a thin film layer at the surface application side SA of the combined membrane and reagent components 1406 and 1404. When present, this thin surface layer can be a few microns in thickness, for example, on the order of less than 5 microns in thickness. Alternatively, the filter/diffuse reflective component 1402 may be entirely subsumed, contained, or impregnated within the combined reagent and membrane components 1404 and 1406.

Figure 15:
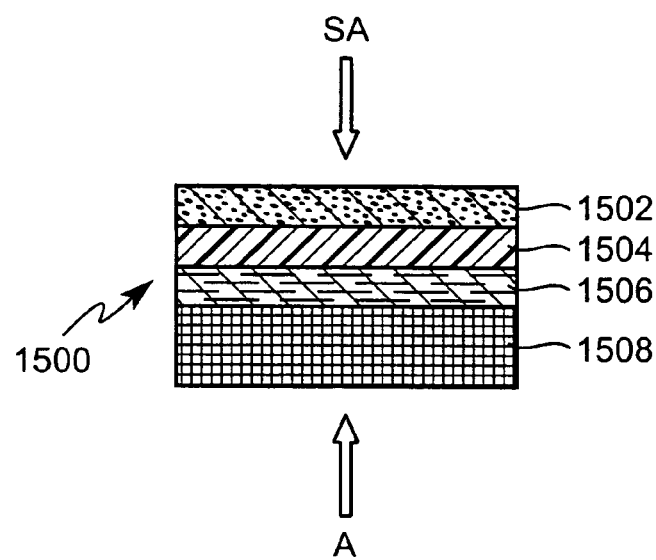
FIG. 15 is a schematic illustration of yet another layered test strip construction according to the present invention.

An additional test pad construction 1500 consistent with the principles of the present invention is illustrated in FIG. 15. According to one aspect, the test pad construction 1500 is comprised of at least four basic components: a filter/diffuse reflective component 1502, a permeable material component 1504, a reagent component 1506, and a membrane component 1508. The general functionality of the test pad 1500 and the functionality of the individual components thereof are similar to that previously described.

The component 1502 may comprise any suitable filter and/or diffuse reflective material. For example, the component 1502 may comprise a zirconium oxide material with or without a polymer binder. When included, the polymer binder is preferably a permeable material. Examples of suitable permeable polymer binders include HPMC and an acrylic resin, such as Elvacite®.

The component 1504 is preferably comprised of a suitable permeable material which can be hydrophobic. The hydrophobic material can comprise any suitable form. According to one example, the component 1504 may comprise a film of a hydrophobic polymeric material, such as PAA. The film can be formed by any suitable technique. For example, a film of PAA is formed by a fast evaporating solvent/PAA mixture. According to one specific example, the mixture may contain 10% by weight (relative to the weight of the solvent) of PAA.

The component 1506 may comprise a suitable reagent material. The reagent material may be combined with a binder. The reagent component may be chosen from any suitable substance or combination of substances, as described above. When present, the binder material comprises a permeable hydrophobic binder material. One suitable example is HPMC.

The membrane component 1508 can be formed from any suitable material. According to one possible construction, the membrane component 1508 is formed from an unwoven fibrous mat. For example, the reagent component 1506 can be spin coated upon the membrane component 1508. As discussed above, the reagent component 1506 may be partially, or entirely, impregnated within the membrane component 1508. Thus, the reagent component 1506 may or may not comprise a thin surface layer formed on top of the membrane component 1508 (the top side being closest to the surface application side SA of the test pad 1500).

The hydrophobic material component 1504 can then be applied. According to one possible technique, the hydrophobic material can be formed as a slurry or mixture with a fast evaporating solvent, such as methanol. The mixture is then coated onto the combined membrane and reagent components 1508 and 1506. Subsequent to evaporation, a thin film of the hydrophobic material is left on top of the combined reagent/membrane component.

The component 1502 may then be applied to the previously described combined components. According to one example, a combination of filter/diffuse reflective material, e.g.— $ZrO_2$, and a polymer binder material, such as the ones described above, may be combined in the form of a slurry or mixture and then coated upon the previously combined components. According to one specific example, a slurry containing up to 10% by weight of $ZrO_2$ may be formed and then spin coated onto the previous combined constituent components 1504, 1506, and 1508. As previously discussed, the component 1502 may be partially or entirely impregnated or subsumed within the previously combined components. Thus, the component 1502 may be indistinguishable from the previously combined components or, may form a thin film or layer on top of the previously combined components.

Figure 16:
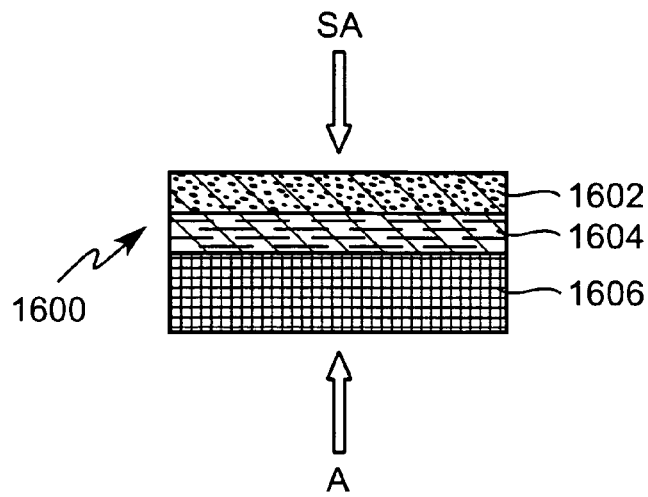
FIG. 16 is a schematic illustration of a further layered test strip construction according to the present invention.

Yet another alternative test pad construction 1600 formed according to the principles of the present invention is illustrated in FIG. 16. The test pad construction 1600 illustrated therein is formed from at least three basic constituent components: a filter/diffuse reflective component 1602, a permeable hydrophobic material component 1604 and a combined reagent/mesh component 1606. The basic functionality of the individual as well as combined constituent components of the test pad construction 1600 is similar to that previously discussed.

The filter/diffuse reflective component 1602 can be formed from any suitable material, and comprise any suitable construction. According to one possible embodiment, the component 1602 comprises a zirconium oxide material, which may optionally be combined with a binder material. When present, the binder material is preferably a permeable hydrophobic binder material such as an acrylic resin. Such material is being commercially available, e.g.—sold as Elvacite®.

Similarly, the permeable hydrophobic material component 1604 can be comprised of any suitable material, and take any suitable form. By way of example, the permeable hydrophobic material can comprise a film or layer. According to one specific example, the permeable hydrophobic material may comprise PAA.

The combined reagent/mesh component 1606, as implied is preferably the combination of two distinct parts or constituents. Namely, a reagent material such as those previously described, as well as a mesh material constituent. Preferably, these constituents are combined into a single, integral component 1606. The mesh material can be formed of any suitable material and take any suitable form. For example, the mesh material can be formed from a woven polyamide material, such as a woven nylon mesh. The mesh may have openings of any suitable dimensions, such as either 30 microns openings or 41 micron openings.

The above-described constituents can be applied to one another or combined in any suitable manner.

According to one specific example, the reagent and the mesh component are combined or integrated by soaking the mesh material in a slurry formed from the reagent material. For example, a slurry or mixture can be formed which comprises 20% by weight HPMC binder material plus a suitable reagent chemistry. The mesh material is soaked in this liquid slurry. The mesh material is then removed and dried, thereby leaving an integrated mesh/reagent component 1606.

The hydrophobic component 1604 can be similarly be applied by any suitable technique. For example, as described above, the hydrophobic material can be applied as a film formed from a fast evaporating solvent, like methanol. According to one specific example, a hydrophobic material, such as PAA is combined with a solvent to form a slurry. According to one embodiment, the slurry may comprise 10% by weight of the PAA material. The solvent is then applied to the combined reagent/mesh component 1606. Upon evaporation of the solvent, a thin film or layer of the hydrophobic material is left behind, thereby forming the hydrophobic material component 1604.

The filter/diffuse reflective component 1602 may similarly be applied by any suitable technique, such as those previously described. According to one aspect example, a zirconium oxide material is added to a hydrophobic binder to form a slurry in an evaporative solvent such as toluene. According to this specific example, the slurry contains approximately 10% by weight of acrylic resin such as Elvacite®. This slurry is then coated onto the combined hydrophobic and reagent/mesh components 1604 and 1606. Any suitable coating technique can be utilized, such as the aforementioned spin coating technique.

According to one possible construction, the filter/diffuse reflective component 1602 is provided in the form of a thin layer or film on top of the combined hydrophobic material and reagent/mesh component 1604 and 1606.

While the present invention has been described by reference to the above-mentioned embodiments, certain modifications and variations will be evident to those of ordinary skill in the art. Therefore, the present invention is limited only by the scope and spirit of the appended claims.

We claim:

1. An arrangement for use in detecting the presence or concentration of an analyte present in bodily fluid, the arrangement comprising:
   (a) an assay pad adapted to receive a sample of the bodily fluid, the assay pad containing a reagent;
   (b) an array of CMOS detectors, each detector adapted to produce a signal indicative of a reaction between the analyte and the reagent; and
   (c) electronics monitoring and interpreting the signals produced by the detectors to estimate the volume of the sample under analysis based on the number of CMOS detectors producing a signal indicative of the reaction between the analyte and the reagent.

2. The arrangement of claim 1, wherein the electronics further comprise at least one corrective algorithm.

3. The arrangement of claim 1, wherein the electronics generate an overall reading based on the signals produced by the individual detectors.

4. The arrangement of claim 1, further comprising a skin penetration member.

5. The arrangement of claim 4, wherein the skin penetration member comprises a microneedle.

6. The arrangement of claim 1, further comprising a chamber for receiving the sample of bodily fluid.

7. The arrangement of claim 6, wherein the assay pad is disposed in the chamber.

8. The arrangement of claim 1, further comprising at least one light source adapted to provide light incident upon the assay pad.

9. The arrangement of claim 1, wherein at least one dimension of the linear array is commensurate to at least one dimension of the assay pad.

10. A method useful in detecting the presence or concentration of an analyte present in bodily fluid, the method comprising:
    (a) introducing a sample of the bodily fluid onto an assay pad, the assay pad containing a reagent;
    (b) monitoring a reaction between the analyte and the reagent, comprising an array of CMOS detectors wherein at least one CMOS detector provides a signal in response to the reaction; and
    (c) monitoring and interpreting the at least one signal to provide an estimate of the volume of the sample under analysis based on the number of CMOS detectors producing a signal indicative of the reaction between the analyte and the reagent.

11. The method of claim 10, wherein step c) further comprises applying at least one corrective algorithm to the at least one signal.

12. The method of claim 10, wherein step c) further comprises generating an overall reading based on the signals produced by the individual detectors.

13. The method of claim 10, further comprising providing a skin penetration member.

14. The method of claim 13, wherein the skin penetration member comprises a microneedle.

15. The method of claim 10, further comprising providing a chamber for receiving the sample of bodily fluid.

16. The method of claim 15, wherein step a) further comprises disposing the assay pad in the chamber.

17. The method of claim 10, further comprising providing light incident upon the assay pad.

18. The method of claim 10, further comprising providing the linear assay with at least one dimension commensurate to at least one dimension of the assay pad.

* * * * *